United States Patent [19]
Faccioli et al.

[11] Patent Number: 5,662,648
[45] Date of Patent: Sep. 2, 1997

[54] METHOD AND APPARATUS FOR THE EXTERNAL SETTING OF FRACTURES

[75] Inventors: Giovanni Faccioli, Monzambano; Daniele Venturini, Veronese, both of Italy

[73] Assignee: Orthofix S.r.l., Bussolengo, Italy

[21] Appl. No.: 526,406

[22] Filed: Sep. 11, 1995

[30] Foreign Application Priority Data

Mar. 15, 1993 [IT] Italy ................... VR93A0021

[51] Int. Cl.$^6$ .................. A61F 5/04; A61B 17/60
[52] U.S. Cl. .................. 606/54; 606/53; 606/57; 606/59
[58] Field of Search .................. 606/53, 54, 57, 606/58

[56] References Cited

U.S. PATENT DOCUMENTS

| | | | |
|---|---|---|---|
| Re. 31,809 | 1/1985 | Danieletto et al. | 128/92 A |
| 4,488,542 | 12/1984 | Helland | 128/84 B |
| 4,628,922 | 12/1986 | Dewar | 128/92 ZW |
| 5,019,077 | 5/1991 | De Bastiani et al. | 606/54 |
| 5,152,280 | 10/1992 | Danieli | 606/57 |
| 5,320,622 | 6/1994 | Faccioli et al. | 606/58 |

FOREIGN PATENT DOCUMENTS

| | | | |
|---|---|---|---|
| 3614305 | 11/1987 | Germany | 606/57 |
| 1650121 | 5/1991 | U.S.S.R. | 606/57 |

Primary Examiner—Michael Buiz
Assistant Examiner—Julian W. Woo
Attorney, Agent, or Firm—Hopgood, Calimafde, Kalil & Judlowe

[57] ABSTRACT

An auxiliary device for use in the external setting of fractures is particularly adapted for use in association with an external axial fixator or splint having bolt-holding clamps with spherical joints for fixing bone bolts or screws which can be implanted in fractured pieces of bone. The auxiliary device comprises a central body which can be elongated axially and has end portions which can be releasably coupled to corresponding bolt-holding clamps on an external axial fixator or splint associated therewith; the said end portions are attached to the central body by means of corresponding hinges having hinge axes (20, 20') which are retained in parallel relation to each other and perpendicular to the axis of the body, and securing means is provided for selecting the orientation of the axes of these hinges, without changing their retained parallel-axis relation, so as to allow the bolt-holding clamps to rotate in a single plane at a time of predetermined position.

16 Claims, 4 Drawing Sheets

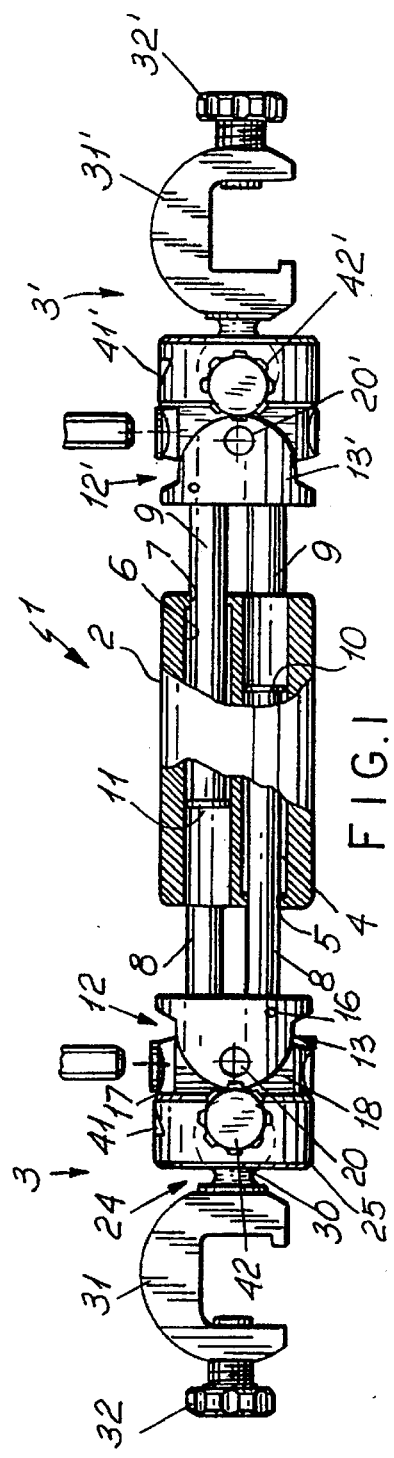

५,६६२,६४८

METHOD AND APPARATUS FOR THE EXTERNAL SETTING OF FRACTURES

DESCRIPTION

1. Field of Application

This invention relates to a method and apparatus for the external reduction of fractures, which are particularly suitable for use in combination with an external splint for bone surgery.

A known method for stabilising pieces of broken bone without the use of orthopaedic plaster provides for the use of so-called external splints. Such devices comprise a set of bone bolts, generally in groups of two, which are inserted into the fractured pieces so that their ends project from the patient's skin and can be anchored to a rigid external member by means of clamps with orientatable joints.

To reduce the fracture the surgeon drills the broken pieces, inserts the bolts and secure them to the corresponding clamps on the splint, and then lines up the edges of the fracture using an X-ray source. Once the fracture has been reduced, the surgeon immobilises the orientable joints of the clamps to hold the bone pieces in a predetermined position, allowing the bone tissue to grow back correctly and the fracture to heal.

Two types of disadvantages can arise while a fracture is being reduced.

The first lies in the difficulty of applying the splint to the bolt-holding clamps because of the fact that the joints are rather bulky and of complex structure. In order to overcome this disadvantage, the reduction is effected by removing the central member of the splint and inserting a suitable device in its stead. After a fracture has been reduced as correctly as possible the clamps are also attached to the splint in the predetermined position, and then are released from the device, which can then be used to reduce other fractures.

This procedure is rather complex and laborious, requires greater surgical time, and runs the risk that the bone bolts may become loose in their corresponding seats. These difficulties may occur again if post-operative action is necessary to correct such misalignments in the broken pieces as may become apparent while healing is in progress.

A second disadvantage lies in the fact that long bones have to be reduced in at least two major planes at right angles to each other, namely the frontal and sagittal planes. Because the image provided by an X-ray source is bidimensional, it is not possible to set a fracture correctly in both planes at the same time. Also, alignment of the pieces in one plane may cause changes in the alignment already achieved in the previous plane.

2. State of the Art

U.S. Pat. No. 4,628,922 (University College London) describes a reduction device for the external fixation of fractures comprising two longitudinally spaced clamps for bone bolts which can be implanted into the broken pieces of a fractured bone; the respective clamps are located at the ends of an extendable rod. Each clamp has means for adjustable rotation with respect to the rod about three axes which are mutually perpendicular and which intersect at a single point located within the bone; and the two points of such clamp-axis intersection are spaced apart longitudinally along the axis of the bone. In practical use, the reduction device is mounted on clamps to effect setting and is only removed after the splint has been fitted.

U.S. Pat. No. 4,488,542 (Helland) discloses a device for the external setting of fractures, comprising end clamps mounted on an extendable bar of polygonal cross-section by means of supports which can be oriented, in two mutually perpendicular planes. Each support comprises a first part which is integral with the bar and a second part which is integral with the clamp. The first part provides an arcuate guide having a radius of curvature which corresponds approximately to the distance between the clamp and the axis of the bone, and an arcuate toothed portion is formed on the outer side of the guide. The second part carries a worm screw which tangentially engages the toothed portion of the arcuate guide of the first part, and can be rotated about an axis which is substantially perpendicular to a geometric radial plane which includes the instantaneous locus of worm-to-tooth engagement. To compensate for slight torsional defects in a fracture, one of the clamps can rotate by a few degrees with respect to its support about a longitudinal axis which is parallel to the axis of the bar.

This Helland device permits accurate adjustment in three planes at right angles to each other, but is has a rather complex and expensive structure that is difficult to use. Also, the excessive size of the orientatable supports does not make it easy to apply the device to small axial splints, and in particular it is not suitable for use on external splints with spherical or universal joints, e.g. of the types described in U.S. Pat. No. Re. 31,809 or in U.S. Pat. No. 5,320,622. In fact, because of the compact and independently adjustably oriented nature of their joints, these types of external splints may remain anchored to the clamps while the fracture is being reduced, providing minimum obstruction to the surgeon, a factor which is particularly advantageous during such subsequent interventions as may be necessary to correct any defects in positioning or alignment, or a defect which may be caused by a post-operative accident.

The reduction of a fracture using the latter type of external splint has the following disadvantage. After fragments of a broken bone have been aligned in a first plane using X-ray viewing, the clamps of the splint are immobilized and the limb is rotated through approximately 90° with respect to the X-ray source, whereupon, the clamps are released, and the fragments are then aligned in a second plane perpendicular to the first. Too often, however, a release of the clamps may lose all trace of the previous position; and it is therefore necessary to repeat the alignment in the two planes, through a process of successive approximations to the optimum, as closely as possible. Such procedures result in increased surgery time and increased X-ray exposure of both the patient and attending medical personnel, with results which are not always satisfactory.

It can therefore be said that splints with spherical joints do not have a "memory" of the initial positioning and therefore do not lend themselves to being easily used with the setting devices currently commercially available.

BRIEF STATEMENT OF THE INVENTION

The main object of this invention is to overcome the above-mentioned disadvantages by means of an auxiliary device for the reduction of fractures, wherein the device can be used in aid of setting an external axial splint both during the initial intervention in the operating theatre and in subsequent out-patient interventions to correct random or accidental positioning errors.

A particular object is to provide an apparatus especially suitable for use with an axial splint having universal or spherical joints so as to allow fractures to be reduced in two mutually perpendicular planes and in one plane at a time, with memory of the position adopted in each plane, so as to reduce operation times and exposure to X-rays. Another particular object is to provide an apparatus for the external reduction of fractures, wherein the apparatus is of simple and compact structure so as to permit great flexibility and ease of use.

The foregoing objects are accomplished by an apparatus for the external reduction of fractures which are particularly suitable for use in association with an external axial splint having bolt-holding clamps with spherical joints for fixing bone bolts which can be implanted in pieces of fractured bone, in which the said apparatus comprises an axially elongatable central body having coupling means at its ends for releasable attachment to corresponding bolt-holding clamps on the external axial splint with which the apparatus is associated, characterised in that the said coupling means are connected to the longitudinal ends of the central body by means of a pair of hinges which have axes which are parallel to each other and perpendicular to the axis of the said body, securing means being provided for the selective orientation of the axes of these hinges so as to permit rotation of the bolt-holding clamps in a plane at a time having a selected position.

Through the abovementioned orientatable hinges, the apparatus according to the invention can easily be used in combination with an axial splint with spherical joints for reducing the fracture in one plane at a time, without any risk of altering the memorized position, because the subsequent rotation performed after the orientation of the hinges has been changed will take place in a plane which is completely different from the first.

Preferably each hinge comprises a fork-member hinged to a connecting block by means of a pin perpendicular to the axis of the central body.

Each fork member can be attached telescopically to one end of the central body by means of longitudinal axial guide means which can vary the total length of the device in a longitudinal direction.

The coupling means may comprise stirrups attached to the corresponding hinges by means of spherical joints equipped with immobilising means.

The stirrups may be provided with fixed bolts to elongate and immobilise a pair of operating handles having terminal jaws which can be engaged on the corresponding bolt-holding clamps of the associated external splint.

In this way the fracture can be reduced without separating the clamps from the central member of the axial splint with spherical joints.

In a particular embodiment each hinge may comprise a fork member hinged to a connecting member by means of a pin perpendicular to the axis of the central body. Every joint may comprise a spherical head housed in a cavity of complementary shape provided in a ferrule connected to a corresponding connection member. Each connection member may be connected to the ferrule by means of a bayonet joint and be provided with means for immobilising the joint.

Each stirrup may have an opening with a securing screw for releasable attachment to a corresponding manual maneuvering member, which can in turn be attached to a corresponding bolt-holding clamp of the external axial splint used in combination with the device. Thus, an orthopaedic surgeon may reduce a fracture by acting manually on the clamps of an external axial splint without separating it from its clamps for the bone bolts, simplifying the reduction procedure and reducing X-ray exposure times.

BRIEF DESCRIPTION OF THE DRAWINGS

In the drawings:

FIG. 1 is a front view in elevation of a fracture reduction device of the invention, in partial cross-section in an axial plane;

FIG. 2 is a plan view of the device of FIG. 1, from above, and in partial cross-section in an axial plane that is perpendicular to the plane of FIG. 1;

FIG. 3 is an exploded front view of an end portion of the device of FIG. 1;

Figure 4:
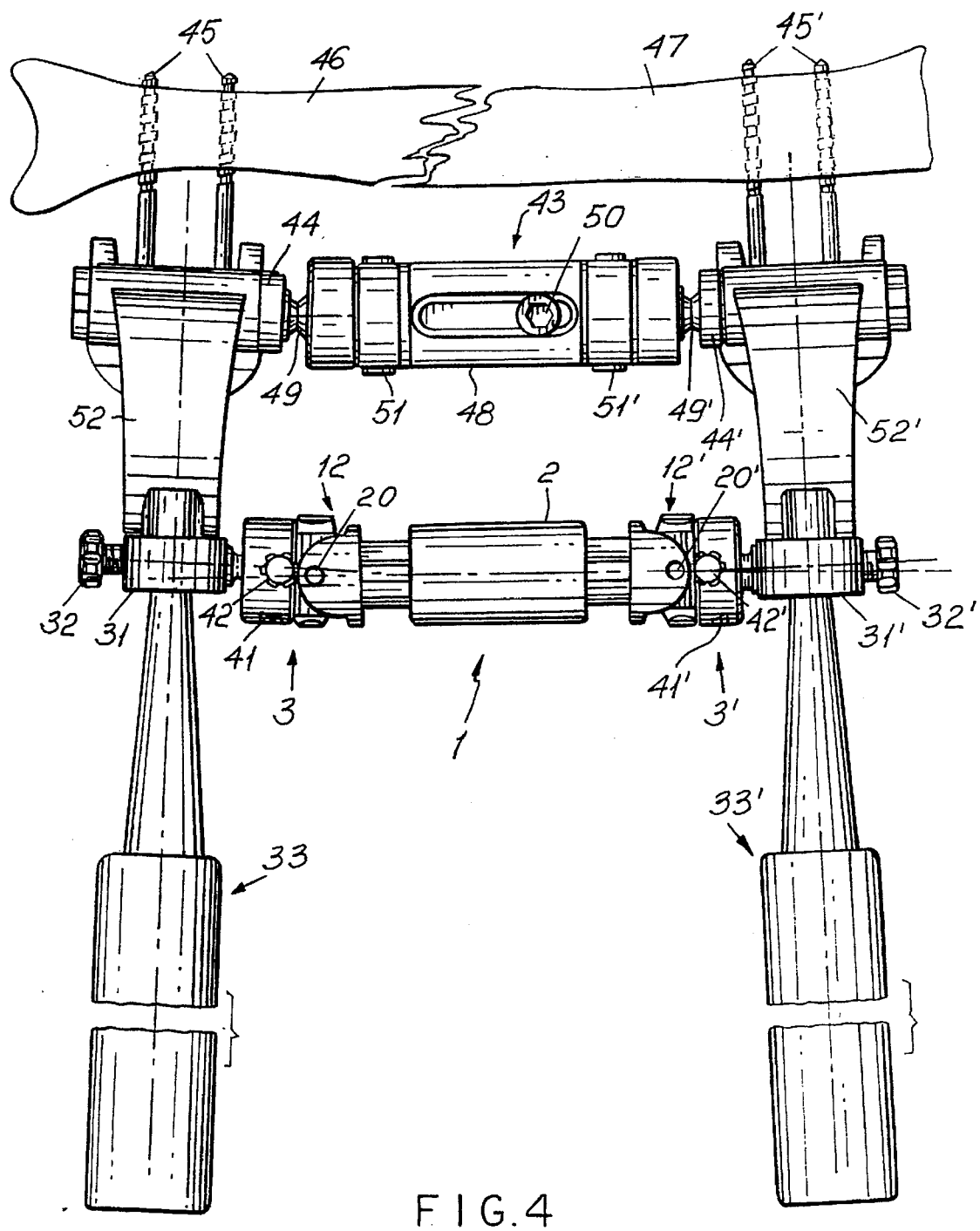
FIG. 4 is a plan view from above of the auxiliary device of FIGS. 1 to 3, attached to an external axial splint having clamped bone screws or bolts inserted in fragments of a fractured bone.

For a better understanding of the invention a preferred but not exclusive embodiment of apparatus for the external reduction of fractures, illustrated by way of a non-restrictive example with the help of the appended drawings, will be described below.

DESCRIPTION OF A PREFERRED EMBODIMENT

In the drawings, an auxiliary device of the invention is generally indicated with the reference number 1, and is seen to comprise a central body 2 with two identical mirror-image end portions 3, 3'. Central body 2 may be a rigid member; it is preferably of cylindrical shape and made of metal, e.g., aluminum alloy, coupled telescopically to end portions 3, 3' by longitudinal guide means for adaptability in the overall length of the device.

The longitudinal guide means may comprise four through-holes, namely, longitudinal bores in two identical pairs, of substantially constant and accurate diameter, parallel to the central-body axis, at radial offset from the central-body axis, and offset angularly from each other by about 90°.

A first pair of diametrically opposed bores 4, corresponding to the left hand end of body 2, has annular stops or radially inward flanges 5 at one longitudinal end of body 2; and the second pair of diametrically opposed bores 6, offset by 90° with respect to the first pair, have annular stops or radially inward flanges 7 at the other longitudinal end of body 2.

Two pairs of cylindrical rods 8, 9, suitably of stainless steel and of diameter slightly less than the inner diameter of annular stops 5, 7, are slidably mounted in the corresponding pairs of bores 4, 6, and project longitudinally from body 2, to the left and to the right, respectively. At the right end of rods 8 a radially outward flange formation 10 has an outer diameter that has running clearance with the diameter of bores 4, being sized for limiting abutment with the stops 5. Similarly, at the left end of rods 9, a radially outward flange formation 11 is sized for running clearance with the diameter of bores 4 and has limiting abutment with stops 7. In this way, the rods 8, 9 are captively guided in their corresponding bores. The projecting ends of shafts 8, 9 which project from body 2 are linked to the end portions 3, 3' by hinges 12, 12' having axes which are retained in parallel relation to each other and perpendicular to the longitudinal axis of the central body.

As the end portions 3, 3' and the corresponding hinges 12, 12' are identical mirror-images, only the left-hand end of the device of FIGS. 1 to 3 will be described. Thus, the component parts of each of these end portions 3, 3' will be identified with corresponding reference numbers, with primed notation for parts at the right-hand end of the device.

In particular, hinge 12 comprises a fork member 13 with side portions 14, 15 attached to the end of rods 8 by means of pins 16; and fork member 13 is hinged to a connecting member 17 by means of a pin 20 that is perpendicular to the longitudinal axis of body 2.

Near its right-hand end, connecting member 17 has a pair of tongues having parallel longitudinal surfaces 18, 19 and inserted between the lateral extensions 14, 15 of fork member 13; and near its left end, connecting member 17 has a collar 21 with a pair of diametrically opposite flat sides 22, 23.

Hinge 12 is connected to end portion 3 by means of a spherical or ball joint 24. The latter is formed in a ferrule 25 having an internal diameter which is less than the diameter of collar 21 of block 19 and a pair of internal radial projections 26, 27 which are diametrically opposite and have flat edges corresponding to flat sides 22, 23 of collar 21 so as to form a bayonet attachment. Thus after flat sides 22, 23 have been aligned with inward projections 26, 27, collar 21 can be inserted into ferrule 25, and then it can be rotated by approximately 90° to secure members 19 to ferrule 27.

Ferrule 25 has a transverse base wall 28 with a central recess 29 designed to receive a spherical head 30. The latter is secured to an end stirrup 31 which is generally U-shaped with a securing screw 32 which is used to immobilize it on a part of complementary shape of an operating handle 33. An identical handle 33' is attached to the other end portion 3' of the equipment by means of an identical stirrup 31' with a securing screw 32' as may be seen in FIGS. 4, 5 and 6.

Member 17 has an axial internal cavity 34 which houses a bush 35 which has one substantially flat end, a transverse substantially cylindrical recess 36 and at the opposite end a cavity 37 of a hemispherical concave shape which is complementary to spherical head 30.

Also there is within member 17 a transverse cylindrical bore 38 into which an eccentric pin 39 is inserted so as to engage recess 36 of bush 35, and at one end there is a hexagonal recess 40 for a hexagon key. When eccentric pin 39 is rotated, this result in axial movement of bush 35 and this member is forced against head 30, which is in turn compressed against recess 29 in ferrule 25, causing it to be locked by friction in spherical joint 24.

It will be noted that on the outer surface of ferrule 25 there is a reference mark 41 which is intended to identify the position of the axis of hinge 12 when the device is fully assembled. A similar reference mark 41' is placed on the other ferrule 25' of joint 24' to identify the orientation of the axis of corresponding hinge 12'. To prevent the separation of members 17 from corresponding ferrules 25, 25' the latter are provided with screws 42, 42' which tighten against a flat 21, 21' on collars 23, 23' of corresponding members 17, 17'.

Figure 5:
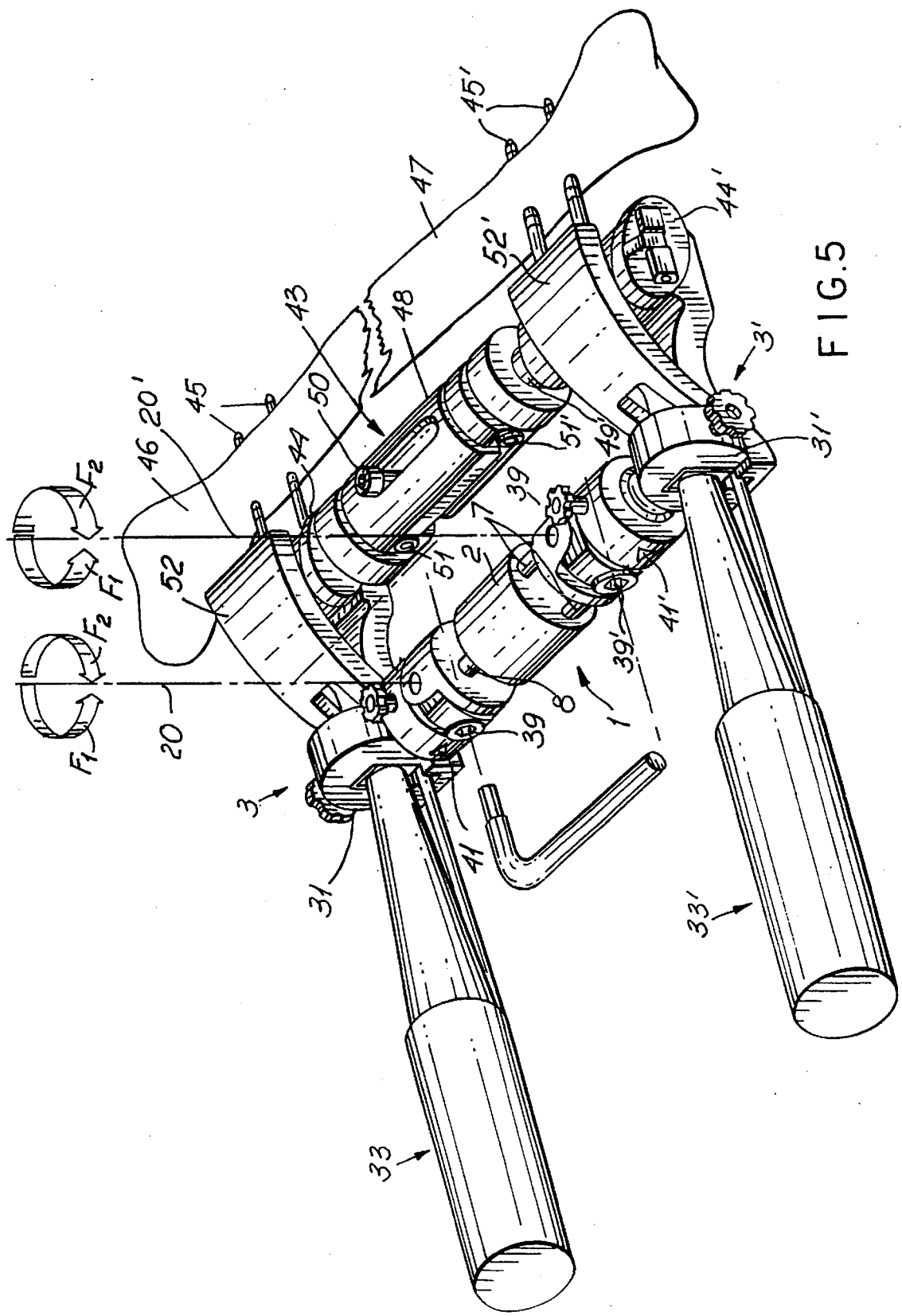
FIG. 5 is a perspective view of the auxiliary device of the invention, in the external-fixation context of FIG. 4 and illustrative of a first stage of operation.
Figure 6:
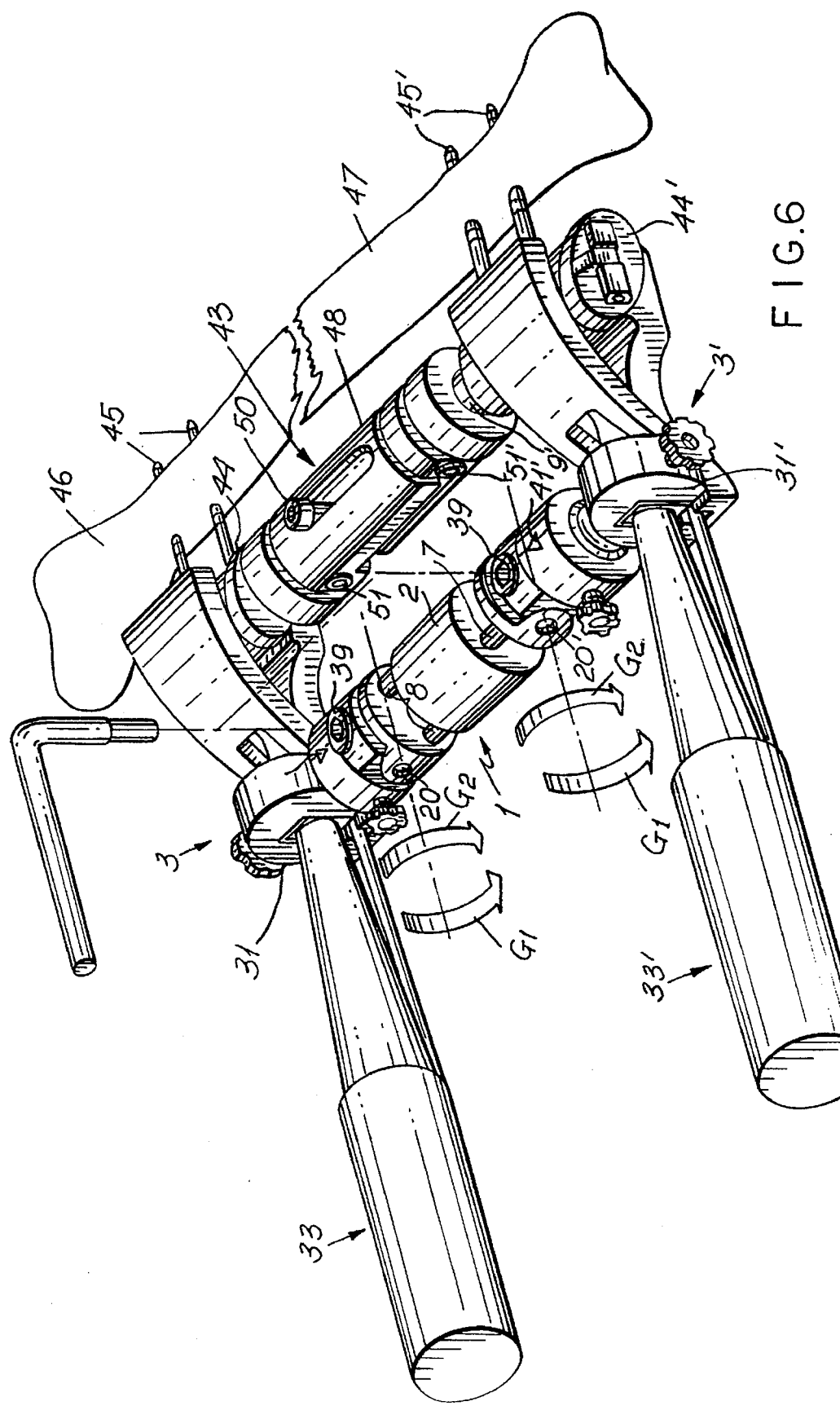
FIG. 6 is a view similar to FIG. 5, to illustrate a second stage of operation.

In FIGS. 4, 5 and 6 and auxiliary apparatus 1 is shown in combination with an axial splint of the type illustrated and described in said U.S. Pat. No. 5,320,622 and generally indicated with the reference number 43. Splint 43 essentially incorporates a pair of clamps 44, 44' for corresponding bone bolts 45, 45' which can be inserted into fractured bone pieces 46, 47 and attached to a central member 48 by means of corresponding end joints 49, 49'. A securing screw 50 is provided on central member 48 to set the axial length, together with eccentric pins 51, 51' to immobilize the corresponding terminal spherical joints.

Handles 33, 33' have terminal jaws 52, 52' which can be immobilized on corresponding clamps, 44, 44' of splint 43, making the end portions 3, 3' of the apparatus 1 integral with fractured bone pieces 46, 47.

In use, after bone bolts 45, 45' have been implanted in bone pieces 46, 47, the surgeon secures them to clamps 44, 44' of splint 43. The fracture can then be reduced using all the movements permitted by the splint, using the apparatus according to the invention.

In particular, to elongate the central member 48, screws 50 can be slackened, and eccentric pins 51, 51' can be rotated by means of a suitable tool not illustrated in the drawings to allow clamps 44, 44' to rotate freely about joints 49, 49'.

Handles 33, 33' attached to clamps 44, 44' by tightening jaws 52, 52' can be used to aid maneuvering and to secure the apparatus 1 to the splint. In turn the apparatus 1 is rigidly secured to handles 33, 33' by means of end stirrups 31, 31'.

At this point the surgeon can reduce the bone in a first plane, e.g. the plane of the paper in FIG. 4, which we will call the horizontal plane. To this end he rotates the eccentric pins 39, 39' of the apparatus 1 using a hexagon key inserted in corresponding hexagonal recesses 40, 40' to release bushes 35, 35' from spherical heads 30, 30' and allow each hinge 12, 12' to rotate freely. After rotating hinges 12, 12' until the axes of each pin 20, 20' and corresponding reference 41, 41' are in the vertical position illustrated in FIGS. 4, 5, eccentric pins 39, 39' are again immobilized. From now on the stirrups, handles and bold holding clamps of the splint can be rotated only in a horizontal plane as indicated by arrows F1 and F2. Using an X-ray source the surgeon can find the best alignment and spacing between bone pieces 46, 47 in that plane, and can then immobilize screw 50 and eccentric pins 51, 51' of splint 43, "remembering" the position adopted in this first plane.

In order to reduce the bone in a second plane perpendicular to the first, the surgeon must release pins 39, 39' from the device and must rotate the hinges through 90° so as to bring the axes of hinges 20, 20' into a horizontal position, as shown in FIG. 6. Then he will again immobilise pins 39, 39' and release splint 43, unscrewing screw 50 and pins 51, 51'. At this point the surgeon can rotate the stirrups, handles and bold holding clamps only in a vertical plane in the directions indicated by arrows G1 and G2 shown in FIG. 6. After having aligned the fracture at best in this plane too making use of X-ray equipment, the surgeon can then make a further check in the previous plane, and finally can immobilise the axial splint in the reduced position.

At the end of the operation, the apparatus can be separated from the clamps on the splint to be used on another patient or for further work on the same fracture at a subsequent time.

From what has been described above it is clear that the apparatus according to the invention achieves the stated objects and in particular permits easy and rapid reduction of a fracture while keeping the splint fixed at all times to the bone pieces. Also it makes it possible to "remember" and maintain the alignment in each plane in which it has been orientated, appreciably reducing setting times and exposure to X-rays. Finally, it becomes possible to act again on a fracture which has already been reduced, without having to make a minimum change in the position of the splint already fitted, all with appreciable simplification in corrective work for any positioning errors or displacements caused by post-operative accidents.

The apparatus described above is susceptible of many modifications and variants, all of which fall within the scope of the invention expressed by the appended claims. All details may be replaced by equivalent technical members which it is intended should also be equally protected.

We claim:

1. Fracture-setting apparatus for the external setting of fractures, adapted for use in association with an external axial splint (43) having bolt-holding clamps (44, 44') with spherical joints (49, 49') for fixing bone bolts which can be implanted into fractured pieces of bone, said fracture-setting apparatus comprising a central body (2) defining an axis, said body being elongatable along said axis and having end portions (3, 3') arranged for releasably coupling to corresponding bolt-holding clamps (44, 44') on the external axial splint (43) associated therewith, the said end portions (3, 3') being attached to the central body (2) by means of corresponding hinges (12, 12') which have hinge axes (20, 20') and means to retain the hinge axes parallel to each other and perpendicular to the axis of the body, and selectively adjustable securing means (39, 39') for selecting the orientation of the axes (20, 20') of said hinges (12, 12') so as to allow the end portions (3, 3') to rotate in an identical single plane at a time of predetermined position.

2. Apparatus according to claim 1, in which each hinge (12, 12') comprises a fork member (13, 13') hinged to a connecting member (17) by means of a pin (20) perpendicular to the axis of the central body (2).

3. Apparatus according to claim 2, in which each fork member (13, 13') is attached telescopically to one end of the said body by means of longitudinal axial guide means (4-11) capable of varying the total length of the central body in a longitudinal direction.

4. Apparatus according to claim 3, in which the said guide means comprise at least one pair of longitudinal rods (8, 9) slidably housed in axial holes (4, 6) in the said central body (2).

5. Apparatus according to claim 2, in which each attachment member (17) for the said hinges is connected to a corresponding coupling stirrup (31, 31') by means of a spherical joint (24, 24') provided with immobilizing means.

6. Apparatus according to claim 5, in which each coupling stirrup (31, 31') is substantially U-shaped with a securing screw (32, 32') for releasable anchoring to a corresponding manual maneuvering member (33, 33') which can in turn be attached to a corresponding bolt-holding clamp (44, 44') on the associated external axial splint (43).

7. Apparatus according to claim 5, in which each spherical joint (24, 24') comprises a spherical head (30, 30') anchored to a corresponding stirrup (31, 31') and inserted in a central hole of complementary shape (29, 29') made in a ferrule (25, 25') which is connected to an adjacent connecting member (17, 17').

8. Apparatus according to claim 5, in which a bush (35, 35') having a hemispherical cavity (37, 37') supported against the countershaped head (30, 30') of the joint (24, 24') is inserted between each connecting member (17, 17') and the ferrule (25, 25').

9. Apparatus according to claim 7, in which the said securing means for each joint comprise an eccentric pin (39, 39') inserted in a transverse hole (38) in a corresponding connecting member (17) in a position such as to force the said bush (35) against the corresponding head (30) of the joint.

10. Apparatus according to claim 6, in which each hinge (12, 12') has a reference marking (41, 41') on an external surface thereof to indicate the position of the axes (20, 20') and to identify their plane of rotation.

11. Method for aligning bolt-holding clamps of an axial splint of elongatable type with universal spherical joints, wherein said clamps and their engaged bolts are respectively anchored to separate pieces of a fractured bone, the method comprising the following steps:

providing an apparatus having a central body defining an axis, said body being elongatable along said axis and being provided with end portions, providing the end portions of said body with coupling means for the rigid attachment of said portions to the bolt-holding clamps of the axial splint in such a way to place the apparatus in a position substantially parallel to the axial splint by means of manual maneuvering members, providing said apparatus with a pair of hinges with orientatable axes which are parallel to each other and perpendicular to the axis of the central body, to join together the end portions of said body with said connection means, selectively positioning and locking the axes of the said hinges in a first orientation to permit rotation of the bolt-holding clamps in a first predetermined plane, without changing the parallel relation of the hinge axes, manipulating the said manual maneuvering members to rotate the connection means in the said first plane, and aligning the clamps using a source of X-rays, selectively positioning and locking the axes of the said hinges in a second orientation perpendicular to the first orientation to allow the bolt-holding clamps to rotate in a second plane at right angles to the first plane, manipulating the said manual maneuvering members to rotate the connection means in the said second plane in such a way as to complete the alignment of the clamps in the said second plane using a source of X-rays, and releasing the coupling means provided at the end portions of the said body after having finally immobilized the axial splint.

12. Fracture-setting apparatus for the external setting of fractures adapted for use in association with an external axial splint (43) having bolt-holding clamps (44, 44') with spherical joints (49, 49') for fixing bone bolts which can be implanted into fractured pieces of bone, said apparatus comprising first and second elongate manipulation-forcep members (33, 33') each of which has at one end means for selectively and rigidly coupling one of said forcep members to one of said bolt-holding clamps (44, 44') with the forcep member extending transversely when attached to one of the bolt-holding clamps, said fracture-setting apparatus further comprising a central body (2) which can be elongated axially and has end portions (3, 3') which can be releasably coupled to the respective manipulation-forcep members and thereby to corresponding bolt-holding clamps (44, 44') of an associated external axial splint, said end portions (3, 3') being attached to the central body (2) by means of corresponding hinges (12, 12') which have hinge axes (20, 20') and means to retain the hinge axes parallel to each other and perpendicular to the axis of the body, and selectively adjustable securing means (39, 39') for selecting the orientation of the axes (20, 20') of said hinges (12, 12') so as to allow the end portions (3, 3') to rotate in an identical single plane at a time of predetermined position.

13. In combination, for use in the external setting of a bone fracture:

(a) an external fixator having an adjustably elongate fixator body, with first and second bone-screw clamps ball-joint connected to the respective longitudinal ends of said body;

(b) first and second elongate manipulation-forcep members, each of which having at one end means for selectively and rigidly clamping one of said forcep members to one of said bone-screw clamps, with the forcep-member extending transverse to the elongation axis of a bone-screw clamp secured thereto; whereby, with said ball-joint connections freed for universal action, a secured bone-screw clamp can be manipulated with respect to the other bone-screw clamp and with respect to the fixator body;

(c) an elongate auxiliary device having lockable forcep-member engaging means at each of its ends, said device comprising elongatable body structure having at each of its longitudinal ends a compound connection to a different one of the forcep-member engaging means, each compound connection comprising a ball-joint connection adjacent one of the forcep-member engaging means and a hinge connection of the ball-joint connection to an end of said body structure, said hinge connections to the respective ends of said body structure being on hinge axes that are retained in parallel relation to each other; and (d) independently releasably settable clamping means for securing a selected universal angle of adjusted ball-joint end connection to each of the respective manipulation-forcep members.

14. Fracture-setting apparatus according to claim 1, in which said central body is longitudinally free within a predetermined longitudinal range to adapt itself to interconnection of said end portions, whereby the longitudinal span between said hinge axes may self-adapt to any extent permitted by said range.

15. Fracture-setting apparatus according to claim 12, in which said central body is longitudinally free within a predetermined range to longitudinally adapt its interconnection of said manipulation-forcep members, whereby the longitudinal span between said forcep members may self-adapt to any extent permitted by said range.

16. Fracture-setting apparatus according to claim 13, in which the body structure of said auxiliary device is longitudinally free within a predetermined range to longitudinally adapt its interconnection of said manipulation-forcep members.

* * * * *